(12) United States Patent
Thompson et al.

(10) Patent No.: US 11,571,653 B2
(45) Date of Patent: Feb. 7, 2023

(54) ETHYLENE SEPARATIONS USING SMALL PORE ZEOLITE SSZ-45

(71) Applicant: CHEVRON U.S.A. INC., San Ramon, CA (US)

(72) Inventors: Joshua A. Thompson, Martinez, CA (US); Dan Xie, El Cerrito, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 17/388,124

(22) Filed: Jul. 29, 2021

(65) Prior Publication Data

US 2022/0062812 A1 Mar. 3, 2022

Related U.S. Application Data

(60) Provisional application No. 63/072,335, filed on Aug. 31, 2020.

(51) Int. Cl.
*B01D 53/047* (2006.01)
*C07C 7/13* (2006.01)

(52) U.S. Cl.
CPC .... *B01D 53/047* (2013.01); *B01D 2253/1085* (2013.01); *B01D 2256/24* (2013.01); *B01D 2257/102* (2013.01); *B01D 2257/108* (2013.01); *B01D 2257/7022* (2013.01)

(58) Field of Classification Search
CPC .............. B01D 53/02; B01D 53/047; B01D 2253/108; B01D 2253/1085; B01D 2256/24; B01D 2257/102; B01D 2257/108; B01D 2257/7022; B01D 2259/40035; B01D 2259/40052; C07C 7/12; C07C 7/13
See application file for complete search history.

(56) References Cited

U.S. PATENT DOCUMENTS

| | | | | |
|---|---|---|---|---|
| 6,033,643 A * | 3/2000 | Yuen | .......................... | C07C 2/12 423/706 |
| 8,926,735 B1 * | 1/2015 | Xie | ..................... | B01D 53/0462 95/139 |
| 2018/0200662 A1 * | 7/2018 | Thompson | ........... | B01D 53/053 |

* cited by examiner

*Primary Examiner* — Youngsul Jeong
*Assistant Examiner* — Jason Y Chong
(74) *Attorney, Agent, or Firm* — Howard Owens

(57) ABSTRACT

The present invention and embodiments thereof provide a process to separate ethylene products from impurities such as nitrogen, hydrogen, ethane, propane and isobutane without the need for distillation processes.

4 Claims, 3 Drawing Sheets

ETHYLENE SEPARATIONS USING SMALL PORE ZEOLITE SSZ-45

FIELD

The present invention and embodiments thereof provide a process to separate ethylene products from impurities such as nitrogen, hydrogen, ethane, propane and isobutane without the need for distillation processes.

BACKGROUND

Ethylene-ethane separations for current commercial applications require the use of very large distillation towers and energy requirements in order to separate ethylene to a polymer-grade level. In the polyethylene plant there are stranded gas streams containing significant ethylene content, ranging from 50 to greater than 90 mol %. Due to the intensive process currently used, these gas streams cannot be recycled or recovered at smaller scales. In prior art, some membrane technologies have been developed that have moderate ethylene membrane selectivity, typically less than 10.

Pressure-swing adsorption (PSA) technology is an alternative technology for recovering stranded ethylene in a polyethylene plant that uses a solid adsorbent material to remove impurities that include ethane, hydrogen, nitrogen and methane gas. The adsorbent selection can function as either an equilibrium-based or kinetic-based separation. In principle, all adsorption processes utilize at least two steps: adsorption or uptake of the target molecule in the adsorbent; and desorption or removal of the same target molecule from the adsorbent. This may be achieved by changes in concentration, pressure, or temperature. In the case of PSA and vacuum-swing adsorption (VSA), pressure changes are used to regenerate the adsorbent. PSA does not require a dehydration step necessarily prior to separation of target components. PSA technology is able to treat stranded ethylene gas to recover ethylene up to a target purity of at least 98 mol % without the use of distillation or other thermally driven separation processes.

It would be desirable to have a PSA or VSA process utilizing an adsorbent material which would require lower vacuum power consumption or elimination of vacuum entirely while allowing for improved recovery of ethylene product. Such a process would enable deployment and competitive use of PSA units to recover stranded ethylene gases.

SUMMARY

In one embodiment a method is provided for removing impurities found in a polyethylene plant from a stranded ethylene gas stream. These impurities include methane, nitrogen, hydrogen and ethane, but may also include propane and isobutane.

A further embodiment of the method includes alternating input of the feed gas stream between at least two beds of adsorbent particles comprising a zeolite SSZ-45 such that the feed gas stream contacts one of the at least two beds at a given time in an adsorption step and a tail gas stream is simultaneously vented from another of the at least two beds in a desorption step. The contact occurs at a feed pressure of from about 50 to about 500 psia for a sufficient period of time to preferentially adsorb ethylene over other impurities in the gas stream. A product gas stream is produced containing no greater than 2 mol % of impurities and at least 98 mol % purity of ethylene. The feed gas stream is input at a feed end of each bed. The product gas stream is removed by depressurization of the bed and desorption of ethylene adsorbed on the zeolite adsorbent SSZ-45. The impurity stream is produced in less than the feed composition of ethylene and utilized as a fuel gas or other gas stream within the polyethylene plant.

DETAILED DESCRIPTION

Figure 1:
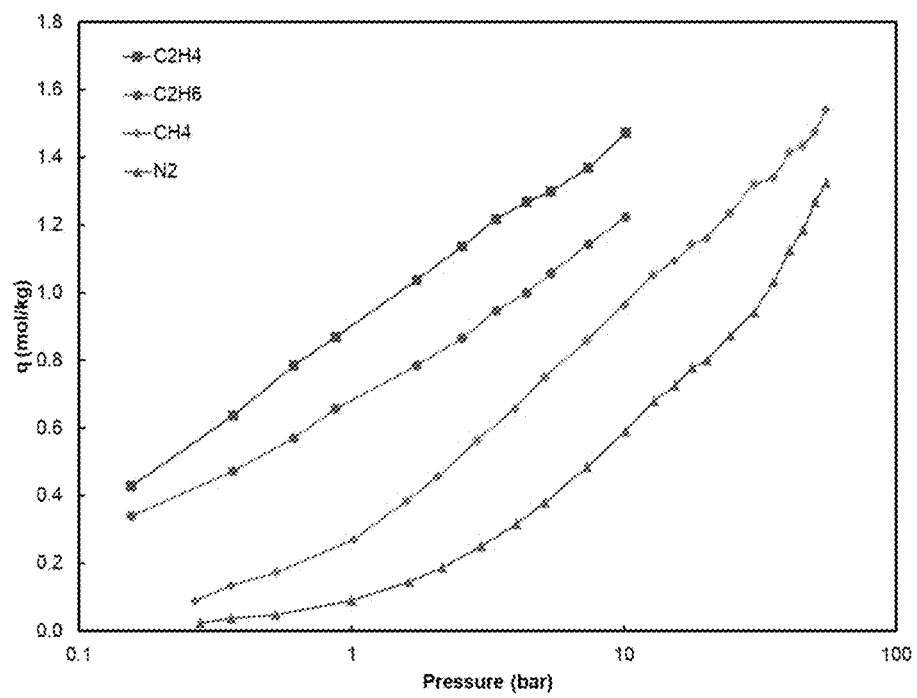
FIG. 1 is a plot of gas adsorption isotherms of C2H4, C2H6, CH4, and N2 on SSZ-45 at 30 degrees C.

The methods of the present disclosure use SSZ-45 zeolite particles as an adsorbent material in a cyclic adsorption process for upgrading ethylene product from at least 50 mol % to at least 98 mol %. The other components in the stream can be ethane and larger hydrocarbons as well as N2, CH4 and H2.

In one embodiment, methods and processes of the present disclosure use alternative adsorbent particles that comprise a zeolite SSZ-45 to remove the contaminants from a feed gas stream. Zeolites are crystalline solid structures made of silicon, aluminum and oxygen that form a framework with cavities and channels inside where cations, water and/or small molecules may reside. Zeolites are crystalline aluminosilicates with open 3D framework structures built of SiO4 and AlO4 tetrahedra linked to each other by sharing all the oxygen atoms to form regular intra-crystalline cavities and channels of molecular dimensions. A defining feature of zeolites is that their frameworks are made up of 4-coordinated atoms forming tetrahedra. These tetrahedra are linked together by their corners and make a rich variety of beautiful structures. The framework structure may contain linked cages, cavities or channels, which are big enough to allow small molecules to enter. The system of large voids explains the consistent low specific density of these compounds. The aluminosilicate framework is negatively charged and can attract positive cations that reside in the cages as a framework ion and can compensate for the negative charge of the framework.

Zeolite SSZ-45 is an example of a synthetic zeolite with an EEI framework type. Molecular sieves are classified by the Structure Commission of the International Zeolite Association (IZA) according to the rules of the IUPAC Commission on Zeolite Nomenclature. According to this classification, framework type zeolites and other crystalline microporous molecular sieves, for which a structure has been established, are assigned a three-letter code and are described in the "Atlas of Zeolite Framework Types," Sixth Revised Edition, Elsevier (2007).

EEI framework type molecular sieves, or zeolites, are characterized by one-dimensional 8-membered-ring pore/channel systems and a large cage. Zeolite SSZ-45 is a small pore zeolite containing channels less than 4 angstrom in diameter and cages less than 20 angstrom in length.

U.S. Pat. No. 6,033,643 discloses an EEI framework type molecular sieve designated zeolite SSZ-45 and its synthesis using N-substituted DABCO cation as a structure directing agent. SSZ-45 is characterized by the presence of 8-ring channels running along the [010] direction and cages delimited by 12-rings aligned along and off the 8-ring channels. The effective pore opening of the oval 8-ring is about 2.2 angstrom×3.9 angstrom but the cavity is about 5.6 angstrom in diameter and 19.8 angstrom long. Thus, SSZ-45 has a small pore opening that can discriminate between small molecules but a large cavity that can give the zeolite high adsorption capacity.

In one embodiment, the zeolite SSZ-45 has a Si:Al mole ratio of 100 or greater, such as from 100 to 400. The Si:Al mole ratio is determined by inductively coupled plasma (ICP) elemental analysis.

In one embodiment the zeolite SSZ-45 is formed into the adsorbent particles by pressing into pellets. In one embodiment, the adsorbent particles can be a component in a membrane that is used for removing the impurities from the feed gas stream that is ethylene-rich. Some examples of mixed-matrix membranes with dispersed adsorbent particles are described in U.S. Pat. No. 6,508,860.

In one embodiment, the zeolite SSZ-45 can be formulated into the adsorbent particles using a combination with other materials, such as binders and/or matrix materials, which provide additional hardness or adsorbent activity to the adsorbent particles. When used, the relative proportions of the zeolite SSZ-45 and other materials may vary widely with the zeolite or molecular sieve content ranging from 1 to 90 wt %, or from 2 to 80 wt % of the adsorbent particles. Previous observations of adsorption rates for three different types of adsorbents have demonstrated diffusion rates for ethylene of less than 1E-05 l/s at 30 C, Rege et al. An unexpected feature of ethylene separation with SSZ-45 is even though the dimensions of the pore window for SSZ-45 are smaller than the size of the ethylene molecule, a fast diffusion rate of ethylene is achieved.

In one embodiment, the adsorbent particles are made from a homogeneous mixture and are not coated particles or made from layers of different materials. An example of how these adsorbent particles can be made is when the adsorbent particles are pressed into pellets from a powder. In one embodiment, the zeolite is mixed with a catalyst support and the zeolite and the catalyst support are ground together into a powder that is a homogeneous mixture. In one embodiment the catalyst support is alumina, such as a pseudo-Boehmite alumina powder. The catalyst support can be inert or can participate in the adsorption performed by the adsorbent particles. Typical catalyst supports include various kinds of carbon, alumina, and silica. In one embodiment, the catalyst support comprises an amorphous silica aluminate. In one embodiment, the catalyst support comprises an amorphous silica aluminate and a second support material.

Examples of the catalyst support or the second support material (when used), can include kieselguhr, alumina, silica, and silica-alumina. Other examples include alumina-boria, silica-alumina-magnesia, silica-alumina-titania and materials obtained by adding other zeolites and other complex oxides thereto. In one embodiment, the catalyst support is porous, and comprises a natural clay or a synthetic oxide. The catalyst support can be selected to provide adequate mechanical strength and chemical stability at the contacting conditions under which the adsorbent particles are employed.

In one embodiment, the catalyst support or the second support material comprises a pseudo-boehmite alumina. Examples of pseudo-boehmite alumina are CATAPAL® high purity aluminas CATAPAL® is a registered trademark of Sasol Limited. The pressed pellets can be broken and sieved to obtain the desired mesh size. In one embodiment, the powder X-ray diffraction (XRD) pattern of the pressed pellets is the same as the original XRD pattern of the zeolite powder prior to it having been pressed into a pellet.

In one embodiment, the method comprises alternating an input of the feed gas stream between at least two beds of the one or more adsorbent particles. In one embodiment, the at least two beds of the one or more adsorbent particles are up to ten beds of the one or more adsorbent particles. The feed gas stream can contact one of the at least two beds at a given time by an adsorption step and a product gas stream can be simultaneously vented from another of the at least two beds by a desorption step to recover high purity ethylene.

In one embodiment, the desorbed high purity ethylene product stream is compressed to from about 500 to 700 psia and recycled to a polyethylene reactor. The contact occurs at a feed pressure of from about 50 to about 500 psia for a sufficient period of time to preferentially adsorb ethylene over other impurities in the gas stream. A product gas stream is produced containing no greater than 2 mol % of impurities and at least 98 mol % purity of ethylene. The feed gas stream is input at a feed end of each bed. The product gas stream is removed by depressurization of the bed and desorption of ethylene adsorbed on the zeolite adsorbent SSZ-45. The impurity stream is produced in less than the feed composition of ethylene and utilized as a fuel gas or other gas stream within the polyethylene plant.

Figure 3:
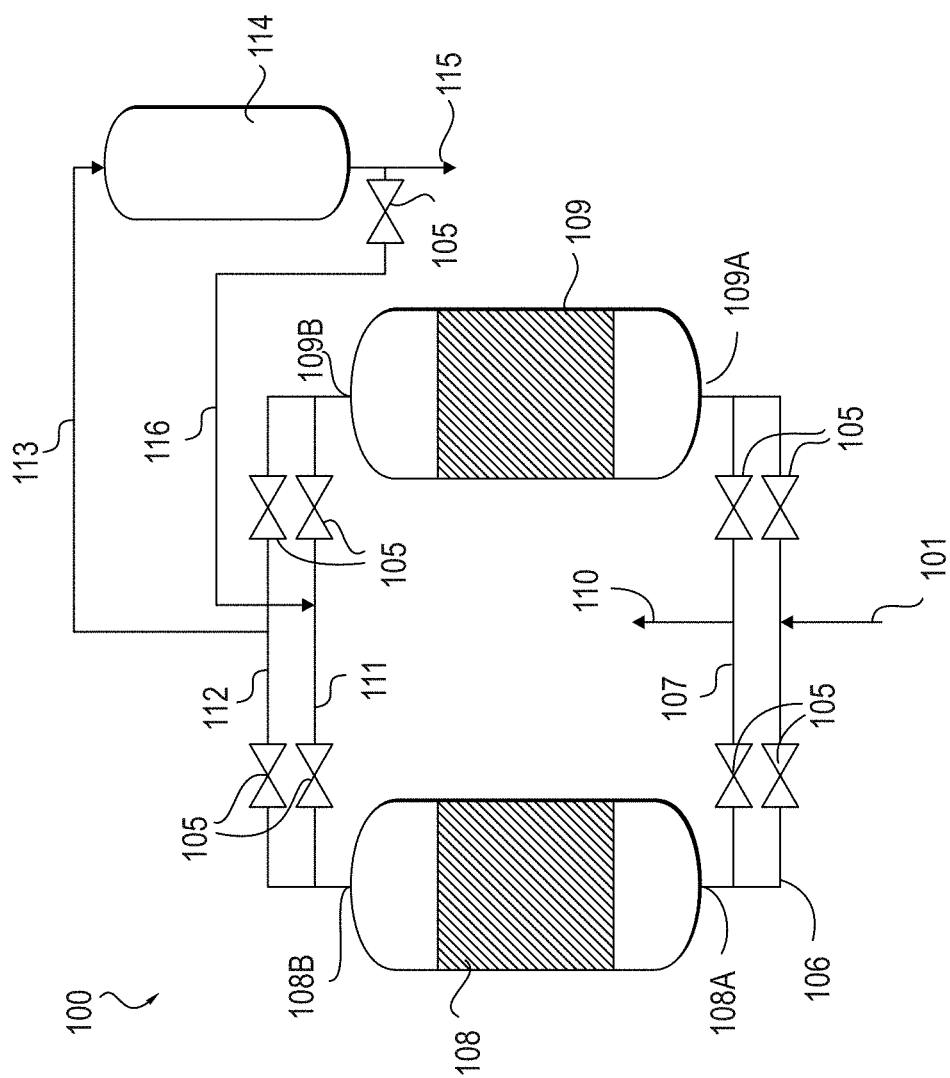
FIG. 3 is a diagram of an exemplary two bed PSA system.

Referring to FIG. 3, here is shown an exemplary two bed PSA system (100) with two beds. In this figure, a feed gas stream (101) is introduced into line (106) having block valves (105) therein. Line (106) connects the first inlet end (108A) to the first adsorption column (108), and also connects the second inlet end (109A) to the second adsorption column (109). A second line (107), is fluidly connected to line (106) and separately connects the first inlet end (108A) to the first adsorption column (108), and also connects the second inlet end (109A) to the second adsorption column (109). Second line (107) has an outlet for tail gas (110). The first adsorption column (108) contains the adsorbent particles described herein and has a first product end (108B). The second adsorption column (109) also contains the adsorbent particles described herein and has a second product end (109B). The first product end (108B) and the second product end (109B) are connected by a third line (111) and by a fourth line (112). The third line (111) and the fourth line (112) contain block valves (105). The fourth line (112) is connected with a fifth line (113), which delivers an intermediate product gas stream to a product gas buffer tank (114). The product gas buffer tank (114) allows for controlled purging and re-pressurization steps. The product gas stream (115) can be provided from the product gas buffer tank (114). The product gas buffer tank is controlled by one or more block valves (105) through a sixth line (116) that connects to the third line (111), as shown.

In one embodiment, wherein the method utilizes two beds of the one or more adsorbent particles, the method further comprises:
(a) following the adsorption step in one of the two beds and a simultaneous desorption step in the other of the two beds, equalizing a pressure of the two beds through the product end of each of the two beds at the end of the adsorption and the simultaneous desorption step; and
(b) re-pressurizing the bed having just completed the simultaneous desorption step by sending a slipstream of the product gas stream through the product end of the bed having just completed the simultaneous desorption step.

Example 1: Synthesis of SSZ-45 Samples 3 mmol of N-cyclopentyl 1,4-diazabicyclo[2.2.2]octane hydroxide (prepared as described in Example 1 of U.S. Pat.

No. 6,033,643), 0.75 g of 1 N KOH and 6 mL of water were added to the Teflon cup of a 23 mL Parr 4745 reactor to yield a clear, basic solution. Silica was then supplied to the reaction mixture by adding 0.92 g of a highly dealuminated FAU framework type zeolite (TOSOH 390HUA, $SiO_2/Al_2O_3$ mole ratio=500). The mixture was sealed and heated at 160° C. for two weeks in an oven equipped with a rotating spit operating at 43 rpm. The autoclave was then removed and allowed to cool to room temperature. The solids were recovered by filtration, washed thoroughly with deionized water and dried.

The resulting product was analyzed by powder X-ray diffraction and shown to be SSZ-45. The product had a silica to alumina mole ratio of greater than 300. Scanning electron micrographs of the resulting product showed crystallites with platelet morphology.

Example 2: Calcination of SSZ-45 Samples

The product of Example 1 was calcined in a muffle furnace under a flow of air heated at 595° C. at a rate of 1° C./min and held at 595° C. for five hours, cooled and then analyzed by powder XRD. Powder XRD confirmed the product as SSZ-45.

Example 3: Pure Component Equilibrium Adsorption

Equilibrium gas adsorption experiments for $C_2H_4$, $C_2H_6$, $CH_4$, and $N_2$ were performed on a HPVA 200-4 port volumetric system. Samples were first activated at 300° C. to obtain the dry weight and then reactivated in the gas adsorption system. Gases used were $C_2H_4$, $C_2H_6$, $CH_4$, $N_2$, and He (all 99.999%). The zeolite was tested from 0-10 bar for both $C_2H_4$ and $C_2H_6$, 0-65 bar for $CH_4$, 0-65 bar for $N_2$, and 0-3 bar for $C_3H_8$.

FIG. 1 shows the equilibrium adsorption results for gas adsorption tests. These represent either majority components or majority impurities found in stranded ethylene gas streams in polyethylene plants. If an adsorbent is capable of separating $C_2H_4$ from $C_2H_6$, $CH_4$, $N_2$ and $C_3H_8$, majority ethylene may be recovered, especially in application of gas mixtures with about 50 mol % ethylene in the feed gas. Because the SSZ-45 sample has a silica-to-alumina molar ratio of greater than 300, the ethylene and ethane adsorption isotherms show little equilibrium-based selectivity at moderate temperatures. In addition, the $N_2$ and $CH_4$ adsorption isotherms show significantly lower affinity compared to either ethylene or ethane, lowering impact of adsorption of ethylene when being removed from these impurities in stranded ethylene gas streams.

Example 4: Kinetic Uptake of SSZ-98 Adsorbents

Figure 2:
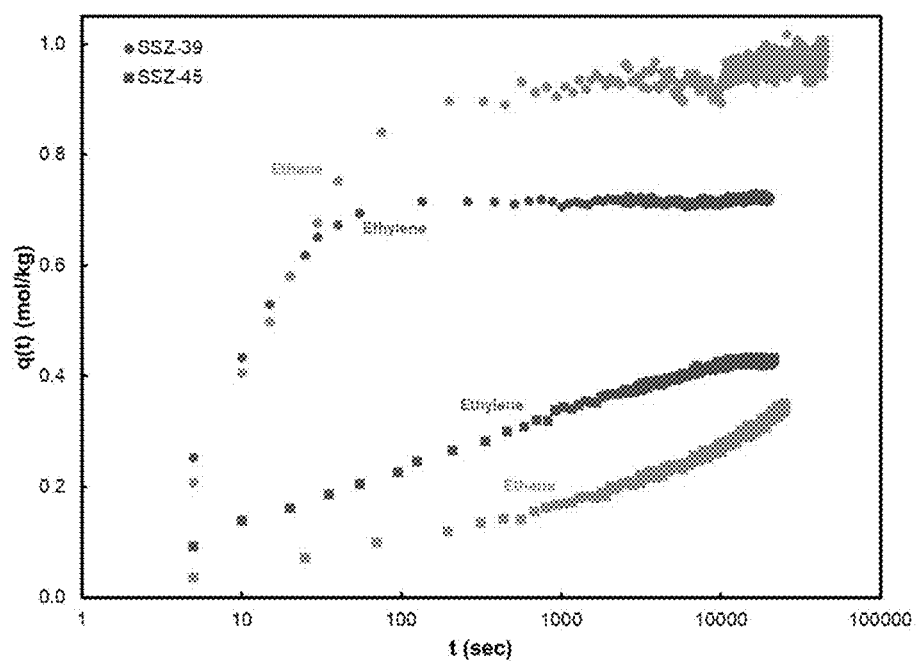
FIG. 2 is a plot of the kinetic uptake of C2H4 and C2H6 on SSZ-45 sample and a comparative zeolite sample, SSZ-39, at 30 degrees C.

Molecular sieving effects in the adsorption uptake of larger molecules found as impurities in ethylene streams such as ethane, propane and isobutane, relative to uptake of ethylene, plays an important role in recovery of ethylene from ethylene-stranded gases. SSZ-45 demonstrates the ability to selectivity adsorb ethylene faster than ethane without any material or synthesis modification, likely due to the unique zeolite pore window and cage structures. This gas pair is important in recovery of ethylene from stranded ethylene-containing gases as molecules with two or more carbons can be difficult to remove if adsorbed onto the adsorbent material. Slow uptake allows the cycling of adsorbent to prevent complete uptake and maintain separation of the slower-adsorbing compounds during adsorption. FIG. 2 shows kinetic uptake of $C_2H_4$ and $C_2H_6$ of SSZ-45 and a comparative zeolite, SSZ-39. As shown in FIG. 2, uptake of $C_2H_4$ is relatively fast for both zeolite materials; however, ethane kinetic uptake in SSZ-45 is comparatively slow compared to SSZ-39.

Combination of both the equilibrium and the kinetic selectivity can yield the overall cyclic kinetic adsorption performance of a material. Table 1 shows the Henry's adsorption constants and diffusion constants calculated from the adsorption equilibrium and kinetics data from FIGS. 1 and 2, respectively, for SSZ-45. The PSA selectivity in Table 1 is described in D. M. Ruthven and S. C. Reyes, "Adsorptive Separation of Light Olefins from Paraffins", Microporous and Mesoporous Materials, 2007, 104, 59-66. SSZ-45 demonstrates that the PSA selectivity exceeds 10, based on the calculated diffusion and adsorption constants.

TABLE 1

Table 1: Summary of adsorption performance properties for C2H4 and C2H6 for SSZ-45.

| Gas | D/r2 (1/sec) | K (mol/kg/bar) | α (C2H4/C2H6) |
|---|---|---|---|
| C2H4 | 1.87e−05 | 0.116 | 4.6 |
| C2H6 | 2.41e−06 | 0.064 | |

D/r2 is the diffusion constant, K is the Henry's adsorption constant and α is the PSA selectivity.

Table 1: Summary of adsorption performance properties for C2H4 and C2H6 for SSZ-45. D/r2 is the diffusion constant, K is the Henry's adsorption constant and a is the PSA selectivity.

The invention claimed is:

1. A method for removing impurities from a feed gas stream of ethylene-containing stranded gas including impurities and ethylene, comprising:
    (a) alternating an input of the feed gas stream between at least two beds of one or more adsorbent particles made from a homogeneous mixture, wherein the one or more adsorbent particles comprise a zeolite SSZ-45;
    (b) wherein the feed gas stream contacts one of the at least two beds at a given time by an adsorption step and a product gas stream is simultaneously vented from another of the at least two beds by a desorption step;
    (c) wherein the contacting of the one of the at least two beds by the feed gas stream occurs at a feed pressure of from about 345 kPa to about 3450 kPa for a sufficient time to preferentially adsorb the ethylene from the feed gas stream and thereby produces the product gas stream during the desorption step containing no greater than about 2 mol % impurities and at least about 98 mol % of the ethylene recovered from the feed gas stream; and
    (d) wherein the feed gas stream is input at a feed end of each of the at least two beds, and an impurity-enriched gas stream is produced after adsorption of the ethylene and removed at the feed end, and wherein the product gas stream is removed at a product end of each of the at least two beds.

2. The method of claim 1, wherein the zeolite SSZ-45 has a Si:Al mole ratio of 100 or greater.

3. The method of claim 1, wherein the method utilizes two beds of the one or more adsorbent particles, and further comprising:
    (a) following the adsorption step in one of the two beds and a simultaneous desorption step in the other of the two beds, equalizing a pressure of the one of the two beds and the other of the two beds through the product end of each of the one of the two beds and the other of the two beds at an end of the adsorption step and the simultaneous desorption step; and (b) re-pressurizing the other of the two beds having just completed the simultaneous desorption step by sending a slipstream of the product gas stream through the product end of the other of the two beds having just completed the simultaneous desorption step.

4. The method of claim 1, wherein the impurities are selected from the group consisting of nitrogen, hydrogen and ethane.

\* \* \* \* \*